(12) United States Patent
Langer

(10) Patent No.: US 8,712,496 B2
(45) Date of Patent: Apr. 29, 2014

(54) ENDOTRACHEAL TUBE

(75) Inventor: Andreas Langer, Waldkirch (DE)

(73) Assignee: Dr. Langer Medical GmbH, Waldkirch (DE)

( * ) Notice: Subject to any disclaimer, the term of this patent is extended or adjusted under 35 U.S.C. 154(b) by 0 days.

(21) Appl. No.: 13/634,067

(22) PCT Filed: Mar. 14, 2011

(86) PCT No.: PCT/IB2011/051057
§ 371 (c)(1),
(2), (4) Date: Sep. 11, 2012

(87) PCT Pub. No.: WO2011/117773
PCT Pub. Date: Sep. 29, 2011

(65) Prior Publication Data
US 2013/0006083 A1 Jan. 3, 2013

(30) Foreign Application Priority Data
Mar. 23, 2010 (DE) .......... 10 2010 016 076

(51) Int. Cl.
*A61B 5/0492* (2006.01)
(52) U.S. Cl.
USPC .......................... 600/380; 600/546
(58) Field of Classification Search
USPC ........................ 600/380, 547, 546
See application file for complete search history.

(56) References Cited

U.S. PATENT DOCUMENTS

| 5,024,228 | A | 6/1991 | Goldstone et al. |
| 6,266,548 | B1 | 7/2001 | Lamade et al. |
| 8,301,239 | B2 * | 10/2012 | Libbus et al. ............ 607/2 |
| 2005/0011519 | A1 | 1/2005 | Sinderby |
| 2005/0159659 | A1 | 7/2005 | Sawan et al. |
| 2010/0145178 | A1 * | 6/2010 | Kartush ............ 600/380 |
| 2011/0245647 | A1 * | 10/2011 | Stanislaus et al. ........ 600/380 |

FOREIGN PATENT DOCUMENTS

| EP | 0 438 863 A1 | 7/1991 |
| WO | 2008/059415 A1 | 5/2008 |

OTHER PUBLICATIONS

English Translation of the International Preliminary Report on Patentability dated Sep. 25, 2012 in corresponding International Patent Application No. PCT/IB2011/051057, filed Mar. 14, 2011.

* cited by examiner

*Primary Examiner* — Lee S Cohen
(74) *Attorney, Agent, or Firm* — Rankin, Hill & Clark LLP

(57) ABSTRACT

An endotracheal tube with a tube part and a contact electrode for bearing on at least one vocal cord of a patient intubated with the tube, wherein, in order to establish and maintain a reliable contact between the vocal cords of the patient and the contact electrode throughout the duration of an operation, provision according to the invention is made for the contact electrode to have at least one conductor loop which at least approximately circumferentially surrounds the tube part in a contact region.

10 Claims, 3 Drawing Sheets

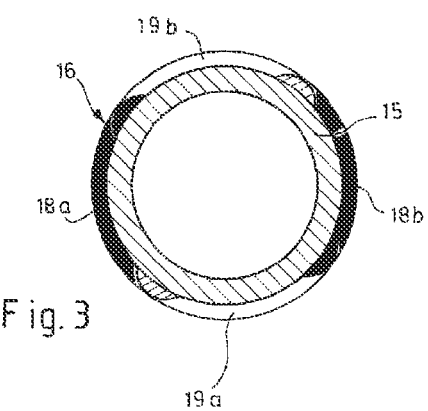
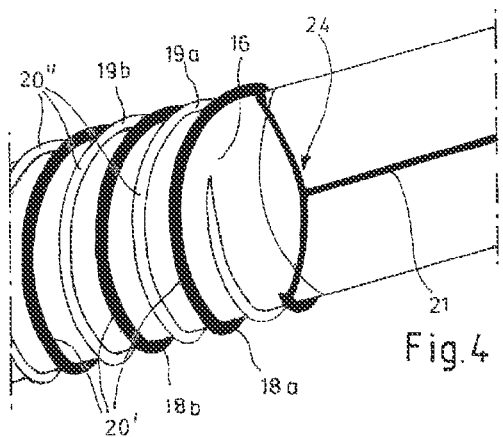

ENDOTRACHEAL TUBE

The invention relates to an endotracheal tube with a tube part and at least one contact electrode for bearing on at least one vocal cord of a patient intubated with the tube.

BACKGROUND OF THE INVENTION

In the case of surgical interventions in the region of the throat of a patient, such as, in particular, during thyroid surgery, there is the risk of injuring the nerves situated in the area of the operation, particularly the recurrent laryngeal nerve, which leads to voice disorders, a loss of voice and/or respiration or swallowing ailments in the patient. There even is a danger to the life of the patient if both sides of the laryngeal nerve branching out of the vagus nerve are injured during goiter operations.

As a result of using functional monitoring of nerves during the operation, it is possible to largely disable this most commonly occurring and dangerous complication even during thyroid surgery, namely injury to the recurrent laryngeal nerve, which is also referred to as recurrent laryngeal paralysis. Whereas use was previously made of intermittent neuro-monitoring by the operator if a nerve at risk was identified and of checking the nerve function, a continuous monitoring method was proposed in the more recent past, in which an electrode is applied for the duration of the operation to the nerve to be monitored, by means of which the nerve is continuously excited or excited at short intervals without manual activity of the operator, and the response signal following this is derived at the target muscle, namely the vocal cords of the patient, and displayed to the operator via a suitable display instrument. In order to be able to determine the response signal at the vocal cords of the patient, a contact electrode that can be brought into contact with the vocal cords is required. To this end, EP 0 438 863 A1 proposes a discharge system on an endotracheal tube, in which two wires are applied opposite to one another and parallel to the tube axis on the tube part, each wire of which should capture the electric activity of respectively one of the two vocal cords. However, reliable discharging is not possible as a result of this because the contact between the vocal cords and the wire electrodes can be lost even in the case of a slight rotation or movement of the tube, and so there is a threat of lesion of the nerve located in the region of the operation and, more particularly, a continuous neuro-monitoring using the known tube cannot reliably be ensured.

Even if the tube electrodes provided on the right-hand and left-hand side of the tube part in the case of known tubes are equipped with a larger contact surface, areas that cannot capture the electric activity of the vocal cords still remain between the two contact electrodes. If the tube part is not placed correctly during intubation, it may be the case that contact between the electrodes and the vocal cords cannot be ensured even in the case of tubes with relatively broad contact electrodes, and so it is no longer possible to measure any signals, which significantly increases the risk of nerve injury as a result of false-negative signal responses.

SUMMARY OF THE INVENTION

It is an object of the invention to provide an endotracheal tube of the type mentioned at the outset, by means of which the contact to the vocal cords can be reliably established and maintained during the whole operation.

According to the invention, this object and others are achieved by virtue of the fact that the contact electrode has at least one conductor loop which at least approximately circumferentially surrounds the tube part in a contact region.

Since the contact electrode surrounds the tube part over at least almost the entire tube circumference by means of the conductor loop, the tube can, during intubation or for the duration of the operation, be rotated relative to the position desired per se, without the contact electrode losing the contact to the vocal cords.

The contact electrode preferably has a plurality of conductor loops, which annularly or helically surround the tube part in the contact region. As a result of this, a plurality of points of contact are potentially created between the contact electrode and the vocal cords of the patient over the length of the contact region, thus ensuring that the tube bears on the vocal cords with at least one conductor loop after intubation of the patient. In a particularly advantageous embodiment of the invention, provision can be made for a plurality of contact electrodes, more particularly for two contact electrodes, the conductor loops of which are arranged alternating with one another in the contact region of the tube part, with the contact electrodes then preferably having different polarities and hence forming at least one bipolar electrode.

It is furthermore advantageous if each contact electrode has a first portion which helically surrounds the tube part and a second portion which helically surrounds the tube part, with the conductor loops of the two electrode portions being arranged alternating with one another in the form of a double helix. In this embodiment, the two electrode portions can be interconnected at a caudal end or a cranial end of the contact region.

The contact region can have a length of between approximately 40 mm and 80 mm, preferably between 50 mm and 70 mm, wherein then, over the length of the contact area, each contact electrode and/or each electrode portion forms between four and twelve conductor loops, preferably between six and ten conductor loops, around the tube part. By way of example, a contact electrode can consist of a conductor wire adhesively bonded onto the tube part in the contact region. However, an embodiment in which the contact electrode(s) is/are formed from an electrically conductive lacquer or polymer material applied to the outside of the tube part, which is for example directly sprayed on the tube part, is particularly advantageous.

The contact electrode(s) is/are connected to at least one contact connector, arranged at the cranial end of the tube part, via at least one connection line arranged along the tube part. Here, the at least one connection line can likewise be formed from electrically conductive lacquer or sprayed on, electrically conductive polymer material. Then, after intubating the patient, a contact cuff or the like can be applied, the latter being connected via cables to the evaluation electronics which display to the operator the response signals to the nerve excitation recorded at the vocal cords of the patient.

An embodiment of the tube according to the invention which can be used in particularly universal fashion is obtained if, in the contact region, the tube part is provided with two contact electrodes, respectively with two electrode portions, with all electrode portions being arranged so as to helically wind around the contact region in the same direction and being arranged alternating with one another. In such a four-fold helical arrangement, the first electrode portion of the first contact electrode, the first electrode portion of the second contact electrode, the second electrode portion of the first contact electrode and the second electrode portion of the second contact electrode expediently lie next to one another in this order. The electrode portions of the first contact electrode can then be interconnected at the cranial end of the contact region and the electrode portion of the second contact electrode can be interconnected at the caudal end of the contact region.

These and other objects, aspects, features, developments and advantages of the invention of this application will become apparent to those skilled in the art upon a reading of the Detailed Description of Embodiments set forth below taken together with the drawings which will be described in the next section.

BRIEF DESCRIPTION OF THE DRAWING

FIG. 3 shows a section along the line III-III of the subject matter of FIG. 2;

FIG. 4 shows a perspective view of a detail IV of the tube according to FIG. 2.

DETAILED DESCRIPTION OF EMBODIMENTS

Figure 1:
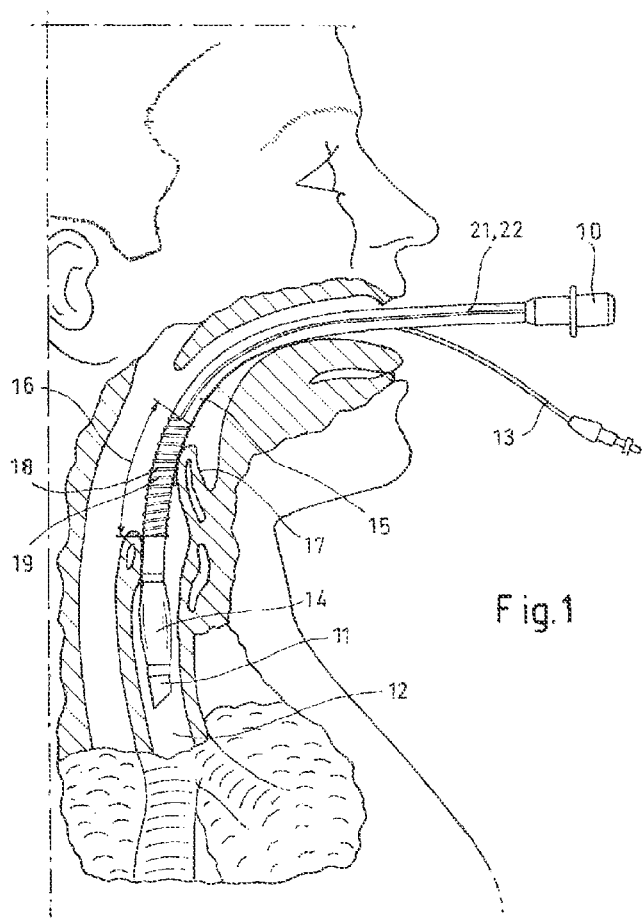
FIG. 1 shows a vertical section of the head of a patient intubated with an endotracheal tube according to the invention.

Referring now to the drawing wherein the showings are for the purpose of illustrating preferred and alternative embodiments of the invention only and not for the purpose of limiting same, the patient illustrated in FIG. 1 is intubated in known fashion using an endotracheal tube 10, the latter with the caudal end 11 thereof extending into the trachea 12 of the patient and being able to be secured and sealed there with respect to the trachea 12 by means of a cuff 14 that can be pumped up via a balloon line 13. Above the cuff 14, the tube part 15 of the tube 10 has a contact region 16, which bears on the vocal cords 17 of the patient (only one of which can be seen in FIG. 1). In the contact region 16, the tube 10 is provided with one or two contact electrodes 18, 19 which are able to measure changes in the electric action potentials of the vocal cords against which they bear. These changes in the electric action potential occur as a response to excitation of the vagus nerve, of the recurrent laryngeal nerve or of the superior laryngeal nerve during intraoperative neuro-monitoring, with use being made thereof when performing operations in the throat region of the patient for monitoring the nerve and preventing inadvertent damage thereto.

Figure 2:
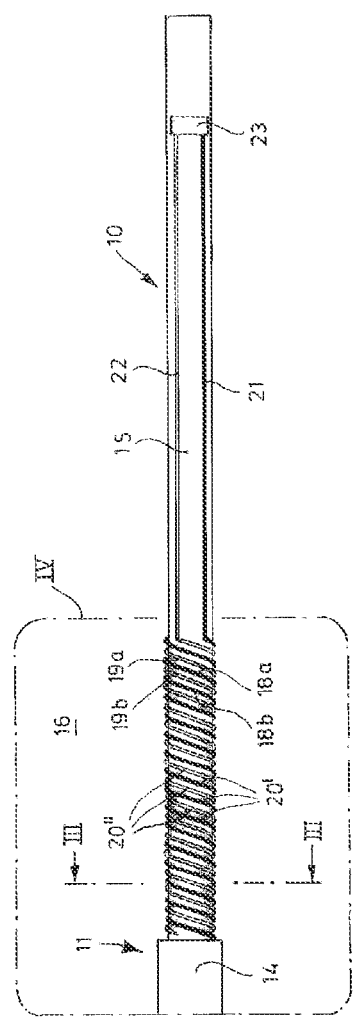
FIG. 2 shows a lateral view of the tube according to the invention in the extended state.

In the embodiments, at least one of the contact electrode(s) 18, 19 is in the contact region 16 of the tube 10 and is the subject matter of the present invention; it can be identified in detail in FIGS. 2 to 4. Accordingly, one or both contact electrodes 18, 19 have at least one conductor loop and, as is shown, can have a plurality of conductor loops 20, which helically surround the tube part 15 in the contact region 16. The arrangement is such that the conductor loops 20' formed by the first contact electrode 18 are always situated between the conductor loops 20" of the second contact electrode 19, i.e. alternate with the latter. Moreover, each of these two contact electrodes 18, 19 respectively forms a first portion 18a, 19a helically surrounding the tube part and a second portion 18b, 19b helically surrounding the tube part, with the conductor loops of the two electrode portions of each contact electrode also being arranged alternating with one another in the form of a double helix and the total of four electrode portions 18a, 19a, 18b, 19b, respectively offset by 90° with respect to one another (FIG. 3), successively winding around the contact region of the tube part. The two electrode portions 18a, 18b of the first contact electrode are interconnected at the cranial end 24 of the tube part, directly above the cuff 14, while the electrode portions 19a, 19b of the second contact electrode 19 merge at the caudal end 11 of the contact region 16.

From the cranial end 24 of the contact region 16, both contact electrodes 18, 19 are connected to a contact connector 23 via respectively one connection line 21 and 22 running along the outside of the tube part 15, which contact connector can be attached to a contact cuff (not illustrated) by connection cables for the purpose of establishing an electrically conductive connection to an evaluation and display apparatus (likewise not illustrated) for the action potentials at the vocal muscles measured by the contact electrodes.

Both the contact electrodes and the connection lines 21, 22 connecting the former to the contact connector 23 consist of an electrically conductive polymer material which is sprayed onto the surface of the tube part and the contact region thereof, has a similar flexibility to the tube part itself and can also undergo the deformations of the latter without being damaged in the process or detaching from the tube part. The electric conductivity or the specific resistance of the contact electrode material used is known from trials and does not change as a result of the deformations which the tube undergoes during handling such that signals resulting from a change in the electric action potential at the vocal muscle are transmitted to the display and evaluation apparatus without falsification.

In the illustrated, preferred exemplary embodiment of the endotracheal tube according to the invention, the contact region 16 has a length of approximately 60 mm, with each contact electrode portion respectively forming eight conductor loops 20 which wind around the contact region. As a result of the multiplicity of possible points of contact with the vocal cords emerging over the length of the contact region, a reliable contact between the contact electrodes and the vocal muscles is ensured at all times. Since the contact region is provided with the conductor loops of the contact electrodes over its whole circumference, not even twisting of the tube in the trachea can lead to the tube part bearing on the vocal cords with a region lacking contact electrodes; this constituted a possible problem in the reliability of the monitoring in the previously known endotracheal tubes used during intraoperative neuro-monitoring.

The invention is not restricted to the illustrated and described exemplary embodiment, but rather various modifications and additions are feasible, without departing from the scope of the invention. By way of example, it is not mandatory for the contact electrodes to helically surround the tube part in the contact region, even though this is particularly advantageous, particularly in the bipolar arrangement of contact electrodes illustrated and described above. Particularly if use is made of a monopolar contact electrode, it is feasible to embody the conductor loops as a closed embodiment which annularly surrounds the contact region, with all conductor loops then being brought into contact with the contact connector via a common, axially running connection line, which runs along the outside of the tube part up to the cuff. A comparable embodiment can also be implemented for bipolar electrodes if the annularly applied conductor loops are not closed in the circumferential direction but rather are interrupted at one point through which the connection line of the respectively other contact electrode can then run, without there being a short circuit with the first electrode. Naturally, the invention can be used not only during continuous neuro-monitoring, but it can also be used in those cases in which the nerve to be monitored is stimulated manually.

Further, while considerable emphasis has been placed on the preferred embodiments of the invention illustrated and described herein, it will be appreciated that other embodiments, and equivalences thereof, can be made and that many changes can be made in the preferred embodiments without departing from the principles of the invention. Furthermore, the embodiments described above can be combined to form yet other embodiments of the invention of this application. Accordingly, it is to be distinctly understood that the foregoing descriptive matter is to be interpreted merely as illustrative of the invention and not as a limitation.

The invention claimed is:

1. An endotracheal tube comprising a tube part and at least one contact electrode for bearing on at least one associated vocal cord of an associated patient intubated with the tube, the at least one contact electrode having at least one conductor loop which at least approximately circumferentially surrounds the tube part in a contact region, the at least one contact electrode has a plurality of conductor loops, which helically surround the tube part in the contact region.

2. The tube as claimed in claim 1, wherein the contact region has a length of between approximately 40 mm and 80 mm and the at least one conductor loop includes between four and twelve conductor loops over the length of the contact region.

3. The tube as claimed in claim 1, wherein the contact region has a length of between 50 mm and 70 mm and the at least one conductor loop includes between six and ten conductor loops over the length of the contact region.

4. An endotracheal tube comprising a tube part and at least one contact electrode for bearing on at least one associated vocal cord of an associated patient intubated with the tube, the at least one contact electrode having at least one conductor loop which at least approximately circumferentially surrounds the tube part in a contact region, the at least one contact electrode has a plurality of conductor loops, which annularly surround the tube part in the contact region.

5. An endotracheal tube comprising a tube part and at least one contact electrode for bearing on at least one associated vocal cord of an associated patient intubated with the tube, the at least one contact electrode having at least one conductor loop which at least approximately circumferentially surrounds the tube part in a contact region, the at least one contact electrode includes a first contact electrode and a second contact electrode, and the at least one conductor loop includes a first plurality of conductor loops and a second plurality of conductor loops respectively, the first plurality of conductor loops and the second plurality of conductor loops being arranged alternating with one another in the contact region of the tube part.

6. The tube as claimed in claim 5, wherein the first contact electrode and the second contact electrode have different polarities and form at least one bipolar electrode.

7. The tube as claimed in claim 5, wherein the first contact electrode and the second contact electrode each has a first portion which helically surrounds the tube part in the contact region and a second portion which helically surrounds the tube part in the contact region, the first plurality of conductor loops and the second plurality of conductor loops of the first and second electrode portions being arranged alternating with one another in the form of a double helix.

8. Tube as claimed in claim 7, wherein the first and second electrode portions are interconnected at a caudal end of the contact region.

9. An endotracheal tube comprising a tube part and at least one contact electrode for bearing on at least one associated vocal cord of an associated patient intubated with the tube, the at least one contact electrode having at least one conductor loop which at least approximately circumferentially surrounds the tube part in a contact region, the at least one contact electrode is two contact electrodes each including two electrode portions, with all electrode portions being arranged so as to helically wind around the contact region in the same direction and being arranged alternating with one another.

10. The tube as claimed in claim 9, wherein the two contact electrodes is a first contact electrode and a second contact electrode, the two electrode portions of the first contact electrode being interconnected at a caudal end of the contact region and the two electrode portions of the second contact electrode being interconnected at a cranial end of the contact region.

* * * * *